US006986984B2

(12) United States Patent
Gawryl et al.

(10) Patent No.: US 6,986,984 B2
(45) Date of Patent: Jan. 17, 2006

(54) USE OF DEFIBRINATED BLOOD FOR MANUFACTURE OF A HEMOGLOBIN-BASED OXYGEN CARRIER

(75) Inventors: Maria S. Gawryl, Charlestown, MA (US); Robert A. Houtchens, Milford, MA (US); William R. Light, Natick, MA (US)

(73) Assignee: Biopure Corporation, Cambridge, MA (US)

( * ) Notice: Subject to any disclaimer, the term of this patent is extended or adjusted under 35 U.S.C. 154(b) by 25 days.

(21) Appl. No.: 10/306,819

(22) Filed: Nov. 26, 2002

(65) Prior Publication Data

US 2003/0113707 A1 Jun. 19, 2003

Related U.S. Application Data

(62) Division of application No. 09/795,821, filed on Feb. 28, 2001, now Pat. No. 6,518,010.

(51) Int. Cl.
*A01N 1/02* (2006.01)
*A61K 38/17* (2006.01)
*C07K 1/00* (2006.01)

(52) U.S. Cl. ............................ 435/2; 424/529; 530/354; 530/363; 530/380; 530/385; 530/829

(58) Field of Classification Search ................ 424/529; 514/6; 530/354, 363, 380, 385, 829
See application file for complete search history.

(56) References Cited

U.S. PATENT DOCUMENTS

| 3,864,478 A | 2/1975 | Bonhard |
| 3,973,001 A | 8/1976 | Jaeger et al. |
| 3,991,181 A | 11/1976 | Doczi |
| 4,001,200 A | 1/1977 | Bonsen et al. |
| 4,001,401 A | 1/1977 | Bonsen et al. |
| 4,053,590 A | 10/1977 | Bonsen et al. |
| 4,061,736 A | 12/1977 | Morris et al. |
| 4,401,652 A | 8/1983 | Simmonds et al. |
| 4,439,357 A | 3/1984 | Bonhard et al. |
| 4,670,417 A | 6/1987 | Iwasaki et al. |
| 4,826,811 A | 5/1989 | Sehgal et al. |
| 4,857,636 A | 8/1989 | Hsia |
| 4,861,867 A | 8/1989 | Estep |
| 5,045,529 A | 9/1991 | Chiang |
| 5,084,558 A | 1/1992 | Rausch et al. |
| 5,189,146 A | 2/1993 | Hsia |
| 5,194,590 A | 3/1993 | Sehgal et al. |
| 5,264,555 A | 11/1993 | Shorr et al. |
| 5,296,465 A | 3/1994 | Rausch et al. |
| 5,296,466 A | 3/1994 | Kilbourn et al. |
| 5,439,882 A | 8/1995 | Feola et al. |
| 5,545,328 A | 8/1996 | Pliura et al. |
| 5,547,873 A | 8/1996 | Magneson et al. |
| 5,691,452 A | 11/1997 | Gawryl et al. |
| 5,691,453 A | 11/1997 | Wertz et al. |
| 5,753,616 A | 5/1998 | Rausch et al. |
| 5,808,011 A | 9/1998 | Gawryl et al. |
| 5,840,852 A | 11/1998 | Rausch et al. |
| 5,854,209 A | 12/1998 | Jacobs, Jr. et al. |
| 5,895,810 A | 4/1999 | Light et al. |
| 2002/0161197 A1 | 10/2002 | Gawryl et al. |

FOREIGN PATENT DOCUMENTS

| GB | 824375 | 11/1959 |
| SU | 455738 | 2/1975 |
| WO | WO 88/03408 | 5/1988 |
| WO | WO 89/06538 | 7/1989 |
| WO | WO 89/12456 | 12/1989 |
| WO | WO 94/22482 | 10/1994 |
| WO | WO 95/22605 | 8/1995 |
| WO | WO 96/29346 | 9/1996 |
| WO | WO 00/21366 | 4/2000 |

OTHER PUBLICATIONS

Alcorta, I., et al., "Influence of the Red Blood Cell Preparation Method on the Efficacy of a Leukocyte Reduction Filter," *Vox Sanguinis*, 71:78–83 (1996).
Baróti Tóth, C. et al., "IgA Content of Washed Red Blood Cell Concentrates," *Vox Sanguinis*, 74:13–14 (1998).
Spain, David A. et al., "Quality Assessment of Intraoperative Blood Salvage and Autotransfusion," *The American Surgeon*, 63:1059–1064 (1997).
Cheung et al., "The Preparation of Stroma–Free Hemoglobin by Selective DEAE–Cellulose Absorption," *Analytical Biochemistry*, 137:481–484 (1984).
Cole et al., "Focal Cerebral Ischemia in Rats: Effect of Hemodilution with α–60 Cross–Linked Hemoglobin on CBF," *J. Cereb. Blood Flow Metab.*, 12(6):971–976 (1992).
De Venuto et al., "Characteristics of stroma–free hemoglobin prepared by crystallization," *J. Lab Clin. Med.*, 89(3):509–516 (1977).
DeVenuto et al., "Appraisal of Hemoglobin Solution as a Blood Substitute," *Surgery, Gynecology, & Obstetrics*, 149(3):417–436 (1979).
Feola et al., "Development of a Bovine Stroma–Free Hemoglobin Solution as a Blood Substitute," *Surgery, Gynecology & Obstetrics*, 157(5):399–408 (1983).
Gibbs, "Artificial Blood Quickens," *Scientific American*, [online] [retrieved on Feb. 14, 2001]. Retrieved from Internet: <URL:http://sciam.com/0996issue/0996techbus4.html>.

(Continued)

Primary Examiner—Ralph Gitomer
Assistant Examiner—Kailash C. Srivastava
(74) Attorney, Agent, or Firm—Hamilton, Brook, Smith & Reynolds, P.C.

(57) ABSTRACT

Red blood cells are purified by defibrinating whole blood and then filtering the defibrinated whole blood, whereby at least a portion of a plasma component is separated from the red blood cells to form a suspension of red blood cells, thereby purifying the red blood cells. Whole blood is defibrinated by, for example, using a chemical coagulating agent or mechanical agitation. Separation of the plasma component from red blood cells can be completed by, for example, diafiltration. The suspension of red blood cells can then be employed to produce a hemoglobin-based oxygen carrier.

11 Claims, 1 Drawing Sheet

OTHER PUBLICATIONS

Hamilton et al., "Preparation of Hemoglobin Solutions for Intravenous Infusion," *J. Exp. Med.*, 86:455–463 (1947).

Sehgal et al., "Polymerized pyridoxylated hemoglobin: A red cell substitute with normal oxygen capacity," *Surgery*, 95(4):433–438 (1984).

Ritter, "Passing a Blood Test," *Chemical & Engineering*, 76:37–44 (1998).

Savitsky et al., "A clinical safety trial of stroma–free hemoglobin," *Clin. Pharmacol. Ther.*, 23(1):73–80 (1978).

Sharma et al., "An Isologous Porcine Promoter Permits High Level Expression of Human Hemoglobin in Transgenic Swine," *Bio/Technology*,12:55–59 (1994).

Teicher et al., "Oxygenation of tumors by a hemoglobin solution," *J. Cancer Res. Clin Oncol.*, 120:85–90 (1993).

Bray et al., "Defibrination of normal human blood in vitro: a method giving a high recovery of untraumatized cells," *British Journal of Haematology*, 35(4):551–559 (1977)(From Database Medline, 1997, Abstract No. NLM871408.

Kay et al., "Rapid recovery of non–hemolyzed serum and untraumatized cells by using a new method of blood defibrination in vitro," *J. of Immunological Methods*, 92(2):251–260 (1986).

Topping et al., "Effects of insulin on the metabolism of the isolated working rat heart perfused with undilated rat blood," *Biochimica et Biophysica Acta*, 844(2):113–118 (1985).

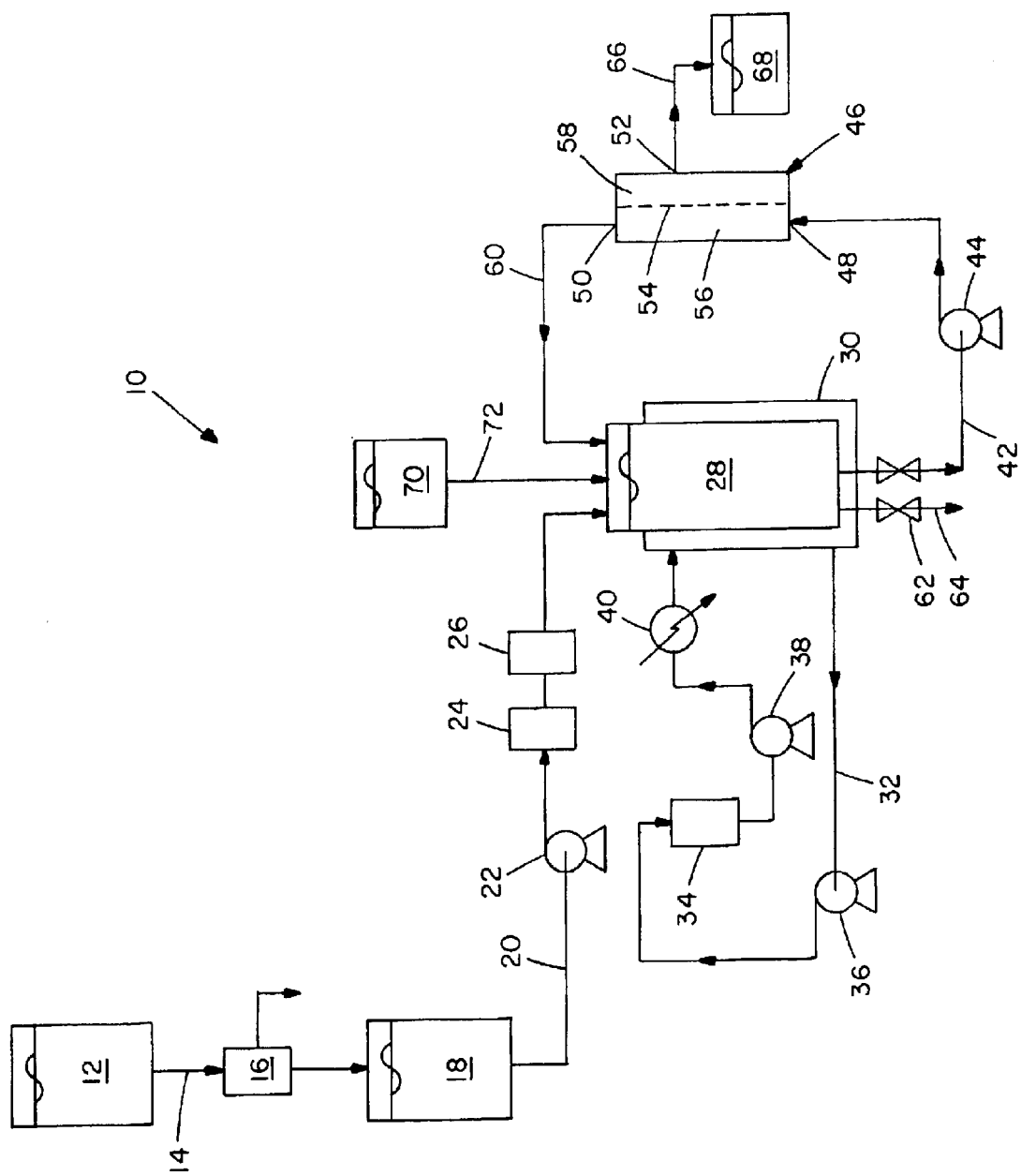

US 6,986,984 B2

USE OF DEFIBRINATED BLOOD FOR MANUFACTURE OF A HEMOGLOBIN-BASED OXYGEN CARRIER

RELATED APPLICATIONS

This application is a Divisional of U.S. application Ser. No. 09/795,821, filed Feb. 28, 2001, now U.S. Pat. No. 6,518,010. The entire teaching of the above application is incorporated herein by reference.

BACKGROUND OF THE INVENTION

The development of hemoglobin-based oxygen carriers has focused on oxygen delivery for use in medical therapies such as transfusions and the production of blood products. Hemoglobin-based oxygen carriers can be used to prevent or treat hypoxia resulting from blood loss (e.g, from acute hemorrhage or during surgical operations), from anemia (e.g., pernicious anemia or sickle cell anemia), or from shock (e.g, volume deficiency shock, anaphylactic shock, septic shock or allergic shock).

Existing hemoglobin-based oxygen carriers include perfluorochemicals, synthesized hemoglobin analogues, liposome-encapsulated hemoglobin, chemically-modified hemoglobin, and hemoglobin-based oxygen carriers in which the hemoglobin molecules are crosslinked. Preparation of hemoglobin-based oxygen carriers includes several purification steps. Among the components that must be removed from collected blood is fibrinogen, which is a soluble protein that is converted into fibrin by the action of thrombin during clotting. Current techniques for processing blood often include addition of chemical agents, such as sodium citrate, to prevent coagulation. However, additional techniques which might, for example, reduce the expense of processing, without diminishing other qualities, such as ultimate product purity, are sought.

SUMMARY OF THE INVENTION

The present invention relates to the use of defibrinated blood for purifying red blood cells, preparing a hemoglobin solution, and preparing a hemoglobin-based oxygen carrier. Chemical clotting agents (such as collagen) and mechanical agitation (such as stirring) are methods used to defibrinate blood. Subsequent cell washing removes plasma proteins that may lead to incompatibility between donor and recipient blood.

In one embodiment, the method for purifying red blood cells includes defibrinating whole blood, the whole blood including red blood cells and a plasma component. Subsequently, the whole blood is filtered to purify the red blood cells and thereby form a red blood cell suspension.

In an embodiment of the method for preparing a hemoglobin solution, whole blood is defibrinated. Red blood cells are separated from the whole blood, and hemoglobin molecules are isolated from the red blood cells to form thereby a hemoglobin solution.

In one embodiment of the method to prepare a hemoglobin-based oxygen carrier, whole blood is defibrinated. Red blood cells are separated from the whole blood. Hemoglobin molecules are isolated and stabilized to form the hemoglobin-based oxygen carrier.

The advantages of this invention are numerous. One advantage is that the invention obviates the need for an anticoagulant solution to be mixed with whole blood (human, bovine, mammalian). Adding an anticoagulant involves manpower and capital for the processes of preparation of high purity water mixing solutions, preparation of citrated collection containers, collection, mixing, and purification. In addition, when shipping blood, generally it is easier to defibrinate blood than it is to build facilities for addition of an anticoagulant at the shipper's location.

BRIEF DESCRIPTION OF THE DRAWINGS

The FIGURE is a schematic of an embodiment of apparatus suitable for conducting the method of the invention.

DETAILED DESCRIPTION OF THE INVENTION

The foregoing and other objects, features and advantages of the invention will be made more apparent from the following more particular description of preferred embodiments of the invention, as illustrated in the accompanying drawing. The drawing is not necessarily to scale, emphasis instead being placed upon illustrating the principles of the invention.

Generally, the invention is a method for purifying blood to form a red blood cell (RBC) suspension, to isolate a hemoglobin solution, and to manufacture a hemoglobin-based oxygen carrier. The method includes defibrinating whole blood. For the purpose of describing the invention, whole blood is considered to be comprised of red blood cells and plasma components.

Referring to the FIGURE, shown therein is one embodiment of apparatus 10 suitable for practicing the method of the invention. Whole blood is collected in vessel 12. Whole blood suitable for use in the invention can be freshly collected or from otherwise outdated sources, such as expired human blood from a blood bank. Further, the whole blood can have been maintained in a frozen and/or a liquid state, although it is preferred that the whole blood has not been frozen prior to use in this method. Examples of suitable whole blood sources include human, bovine, ovine, porcine, other vertebrates and transgenically-produced hemoglobin, such as the transgenic Hb described in *BIO/TECHNOLOGY,* 12: 55–59 (1994), the teachings of which are incorporated herein by reference in their entirety. The blood can be collected from live or freshly slaughtered animal donors. One method for collecting bovine whole blood is described in U.S. Pat. Nos. 5,084,558 and 5,296,465, issued to Rausch et al., the teachings of which are incorporated by reference in their entirety.

The whole blood is defibrinated in vessel 12 by a suitable method. Defibrinating the blood sets off the clotting cascade to remove artificially the fibrin molecules involved in the formation of blood clots. Defibrination can be induced by chemical or mechanical means. Chemical coagulating agents are defined herein as substances that induce clotting. For example, collagen induces coagulation so that when there is an external wound, a fibrin clot will stop blood from flowing. Artificially exposing blood to collagen will cause the formation of fibrin clots, which can be removed to produce defibrinated blood.

In one embodiment, the blood is defibrinated by exposure to a coagulating agent. Examples of coagulating agents are collagen, tissue extract, tissue factor, tissue thromboplastin, anionic phospholipid, calcium, negatively charged materials (e.g., glass, kaolin, some synthetic plastics, fabrics). A preferred clotting agent is collagen.

The whole blood is exposed to the clotting agent for a period of time sufficient to cause essentially all fibrin in the blood to be converted into a fibrin clot. The appropriate time is determined by the point at which fibrin molecules apparently stop polymerizing. Chemical defibrination, defined herein as defibrination that is induced by exposure to a chemical coagulating agent, is conducted at a suitable temperature, preferably a temperature in a range of between about 4° C. and about 40° C.

In another embodiment, mechanical agitation, such as stirring, also has the effect of initiating the clotting cascade. After stirring until fibrin polymerization apparently ceases, it is possible to remove the accumulated fibrin to complete defibrination. Mechanical defibrination, defined herein as defibrination induced by agitating the blood solution, is conducted at a suitable temperature, and preferably at a temperature in a range of between about 4° C. and about 40° C.

Fibrin is then removed from the whole blood by a suitable means. An example of a suitable means is by directing the whole blood, including the fibrin, from vessel 12, through line 14 and strainer 16. A 60 mesh screen is an example of a suitable strainer. Fibrin is collected at strainer 16 and the remainder of the whole blood is directed to vessel 18. Optionally, or alternatively to the use of a strainer, cheesecloth or polypropylene filters can be employed to remove large debris, including fibrin.

As shown in the FIGURE, whole blood is directed from vessel 18 through line 20 by pump 22 and through first filter 24 and second filter 26 to vessel 28. In one embodiment, first filter 24 and second filter 26 are polypropylene filters. In a particularly preferred embodiment, first filter 24 has a permeability of about 800 µm, and second filter 26 has a permeability of about 50 µm. Removal of essentially all of the fibrin by first filter 24 and second filter 26 completes the defibrination step.

The whole blood is maintained at a suitable temperature in vessel 28. Preferably, the whole blood is maintained at a temperature in a range of between about 4° C. and about 15° C. The temperature of whole blood in vessel 28 is maintained by recirculation of a suitable medium, such as ethylene glycol, through jacket 30 at vessel 28. Recirculation of medium through jacket 30 is maintained by line 32, reservoir 34, pumps 36, 38 and chiller, or refrigeration unit, 40.

Thereafter, the whole blood is filtered, whereby at least a portion of the plasma component is separated from the red blood cells to form a red blood cell suspension, thereby purifying the red blood cells. Preferably, the whole blood is filtered by diafiltration.

In one embodiment, diafiltration is conducted by diverting whole blood from vessel 28 through line 42 and pump 44 to diafiltration module 46. Diafiltration module 46 includes inlet 48, retentate outlet 50 and permeate outlet 52. Membrane 54 partitions retentate portion 56 of diafiltrate module 46 from permeate portion 58 of diafiltrate module 46. Preferably, membrane 54 has a permeability limit in a range of between about 0.01 µm and about 5 µm.

A portion of the plasma component of whole blood in diafiltrate module 46 passes across membrane 54 from retentate portion 56 to permeate portion 58, thereby purifying red blood cells at retentate portion 56. Purified red blood cells are directed through retentate outlet 50 and line 60 back to vessel 28. Purified blood can be collected from vessel 28 through valve 62 to line 64 for further processing. Plasma that permeates membrane 54 can be directed from permeate portion 58 of diafiltration module 46 through line 66 and collected from vessel 68. Blood recirculating through vessel 28 and diafiltrate module 46 can be sampled at sampling ports (not shown) in line 42 or line 60.

Preferably, prior to filtering whole blood to remove at least a portion of the plasma component, a liquid is added to the whole blood in vessel 28 from vessel 70 and line 72 to dilute its concentration. In one embodiment, the whole blood is diluted to a concentration in a range of between about 25% and about 75% of its initial concentration (before dilution), by volume. Concentration then can reduce the volume back to the original concentration or more. Generally, the process of adding a liquid to the whole blood and then removing at least a portion of the liquid, is referred to as "cell washing."

In one embodiment, cell washing includes the processes of dilution and diafiltration in a continuous filtration operation; a saline/citrate solution is added to the filter retentate to maintain a constant volume in the recirculation tank. The result is a reduction in the concentration of microfiltration membrane-permeable species (including membrane-permeable plasma proteins). Subsequent reconcentration of the diluted blood solution back to the original volume produces a purified blood solution.

In a preferred embodiment, the blood solution is washed by diafiltration or by a combination of discrete dilution and concentration steps with at least one solution, such as an isotonic solution, to separate red blood cells from extracellular plasma proteins, such as serum albumins or antibodies (e.g., immunoglobulins (IgG)). Preferably, the isotonic solution includes an ionic solute or is aqueous. It is understood that the red blood cells can be washed in a batch or continuous feed mode.

Acceptable isotonic solutions are known in the art and include solutions, such as a citrate/saline solution, having a pH and osmolarity which does not rupture the cell membranes of red blood cells and which displaces the plasma portion of the whole blood. The blood may be diluted to a concentration in the range between about 25% and 75% of the original concentration. A preferred isotonic solution has a neutral pH and an osmolarity-between about 285–315 mOsm. In a preferred embodiment, the isotonic solution is composed of an aqueous solution of sodium citrate dihydrate (6.0 g/l) and of sodium chloride (8.0 g/l).

In one method, the whole blood is diafiltered across a membrane having a permeability limit in the range of between 0.2 µm and about 2.0 µm. Alternate suitable diafilters include microporous membranes with pore sizes that will separate RBCs from substantially smaller blood solution components, such as a 0.1 µm to 0.5 µm filter (e.g., a 0.2 µm hollow fiber filter, Microgon Krosflo II microfiltration cartridge). During cell washing, fluid components of the blood solution, such as plasma, or components which are significantly smaller in diameter than RBCs pass through the walls of the diafilter in the filtrate. Erythrocytes, platelets and larger bodies of the blood solution, such as white blood cells, are retained and mixed with isotonic solution, which is added continuously or batch-wise to form a dialyzed blood solution.

Concurrently, a filtered isotonic solution is added continuously (or in batches) as makeup to maintain volume of filtrate to compensate for the portion of the solution lost across the diafilter. In a more preferred embodiment, the volume of blood solution in the diafiltration tank is initially diluted by the addition of a volume of a filtered isotonic solution to the diafiltration tank. Preferably, the volume of isotonic solution added is about equal to the initial volume of the blood solution.

In an alternate embodiment, the blood is washed through a series of sequential (or reverse sequential) dilution and concentration steps, wherein the blood solution is diluted by adding at least one isotonic solution, and is concentrated by flowing across a filter, thereby forming a dialyzed blood solution.

Cell washing generally is considered to be complete when the level of plasma proteins contaminating the red blood cells has been substantially reduced (typically at least about 90%). Additional washing may further separate extracellular plasma proteins from the RBCs. For instance, diafiltration with six volumes of isotonic solution may be sufficient to remove at least about 99% of IgG from the blood solution.

Potential foulants of the membrane could cause problems with washing, such as slow manufacturing runs, which may be minimized by using new membranes for each run of washing. However, it is still possible to make an effective hemoglobin-based oxygen carrier, despite potential membrane foulants. Small fibrin molecules can be problematic and may foul the filter if they accumulate on the surface of a membrane with a permeability of 0.1 to 5 $\mu$m and thus block the pores. A narrower range in which the foulants can be problematic is 0.2 to 0.4 $\mu$m. Defibrinating (mechanical, chemical, any kind) could cause red blood cell lysing. Red blood cells, white blood cells, or platelets that have broken open might stick to the filter.

In another embodiment of the invention, it is possible to defibrinate blood that has already been citrated by saturating the citrated blood with a divalent cation, and then defibrinating the solution, similar to the means by which uncitrated blood would be processed. The preferred divalent cation is calcium.

To prepare a hemoglobin blood solution, the purified blood sample can be further processed to isolate the hemoglobin molecules. The resulting dialyzed blood solution is exposed to means for separating red blood cells in the dialyzed blood solution from white blood cells and platelets, such as by centrifugation. It is understood that other methods generally known in the art for separating red blood cells from other blood components can be employed. For example, one embodiment of the invention separates red blood cells by sedimentation, wherein the separation method does not rupture the cell membranes of a significant amount of the RBCs, such as less than about 30% of the RBCs, prior to red blood cell separation from the other blood components.

Following purification of the red blood cells, the RBCs are lysed, resulting in the production of a hemoglobin (Hb) solution. Methods of lysis include mechanical lysis, chemical lysis, hypotonic lysis or other known lysis methods which release hemoglobin without significantly damaging the ability of the Hb to transport and release oxygen.

Following lysis, the lysed red blood cell phase is then ultrafiltered to remove larger cell debris, such as proteins with a molecular weight above about 100,000 Daltons. The hemoglobin is then separated from the non-Hb components of the filtrate.

Methods of ultrafiltration and methods of separating Hb from non-Hb components by pH gradients and chromatography are further described in U.S. Pat. No. 5,691,452, filed Jun. 7, 1995, which is incorporated by reference in its entirety.

The Hb eluate is then preferably deoxygenated prior to polymerization to form a deoxygenated Hb solution (hereinafter deoxy-Hb) for further processing into a hemoglobin-based oxygen carrier. In a preferred embodiment, deoxygenation substantially deoxygenates the Hb without significantly reducing the ability of the Hb in the Hb eluate to transport and release oxygen, such as would occur from formation of oxidized hemoglobin (metHb). Alternatively, the hemoglobin solution may be deoxygenated by chemical scavenging with a reducing agent selected from the group consisting of N-acetyl-L-cysteine (NAC), cysteine, sodium dithionite or ascorbate.

The method of deoxygenation is further described in U.S. Pat. No. 5,895,810, filed Jun. 7, 1995, which is incorporated herein by reference in its entirety.

The deoxygenated hemoglobin solution can be further processed into a hemoglobin-based oxygen carrier. As defined herein, a "hemoglobin-based oxygen carrier" is a hemoglobin-based composition suitable for use in humans, mammals, and other vertebrates, which is capable of transporting and transferring oxygen to vital organs and tissues, at least, and can maintain sufficient intravascular oncotic pressure, wherein the hemoglobin has been isolated from red blood cells. A vertebrate is as classically defined, including humans, or any other vertebrate animals which uses blood in a circulatory system to transfer oxygen to tissue. Additionally, the definition of circulatory system is as classically defined, consisting of the heart, arteries, veins and microcirculation including smaller vascular structures such as capillaries.

"Stable polymerized hemoglobin", as defined herein, is a component of a hemoglobin-based oxygen carrier composition which does not substantially increase or decrease in molecular weight distribution and/or in methemoglobin content during storage periods at suitable storage temperatures for periods of about two years or more. Suitable storage temperatures for storage of one year or more are between about 0° C. and about 40° C. The preferred storage temperature range is between about 0° C. and about 25° C.

A suitable low oxygen environment, or an environment that is substantially oxygen-free, is defined as the cumulative amount of oxygen in contact with the hemoglobin-based oxygen carrier, over a storage period of at least about two months, preferably at least about one year, or more preferably at least about two years, which will result in a methemoglobin concentration of less than about 15% by weight in the hemoglobin-based oxygen carrier. The cumulative amount of oxygen includes the original oxygen content of the hemoglobin-based oxygen carrier and packaging in addition to the oxygen resulting from oxygen-leakage into the hemoglobin-based oxygen carrier packaging.

Throughout this method, from RBC collection until hemoglobin polymerization, blood solution, RBCs and hemoglobin are maintained under conditions sufficient to minimize microbial growth, or bioburden, such as maintaining temperature at less than about 20° C. and above 0° C. Preferably, temperature is maintained at a temperature of about 15° C. or less. More preferably, the temperature is maintained at 10±2° C.

In this method, portions of the components for the process of preparing a stable polymerized hemoglobin-based oxygen carrier are sufficiently sanitized to produce a sterile product. Sterile is as defined in the art, specifically, in the United States Pharmacopeia requirements for sterility provided in USP XXII, Section 71, pages 1483–1488. Further, portions of components that are exposed to the process stream, are usually fabricated or clad with a material that will not react with or contaminate the process stream. Such materials can include stainless steel and other steel alloys, such as Hasteloy.

In one embodiment, polymerization results from intramolecular cross-linking of Hb. The amount of a sulfhydryl compound mixed with the deoxy-Hb is high enough to increase intramolecular cross-linking of Hb during polymerization and low enough not to significantly decrease intermolecular cross-linking of Hb molecules, due to a high ionic strength. Typically, about one mole of sulfhydryl functional groups (—SH) are needed to oxidation-stabilize between about 0.25 moles to about 5 moles of deoxy-Hb.

Optionally, prior to polymerizing the oxidation-stabilized deoxy-Hb, an appropriate amount of water is added to the polymerization reactor. In one embodiment, an appropriate amount of water is that amount which would result in a solution with a concentration of about 10 to about 100 g/l Hb when the oxidation-stabilized deoxy-Hb is added to the polymerization reactor. Preferably, the water is oxygen-depleted.

The temperature of the oxidation-stabilized deoxy-Hb solution in the polymerization reactor is raised to a temperature to optimize polymerization of the oxidation-stabilized deoxy-Hb when contacted with a cross-linking agent. Typically, the temperature of the oxidation-stabilized deoxy-Hb is about 25 to about 45° C., and preferably about 41 to about 43° C. throughout polymerization. An example of an acceptable heat transfer means for heating the polymerization reactor is a jacketed heating system which is heated by directing hot ethylene glycol through the jacket.

The oxidation-stabilized deoxy-Hb is then exposed to a suitable cross-linking agent at a temperature sufficient to polymerize the oxidation-stabilized deoxy-Hb to form a solution of polymerized hemoglobin (poly(Hb)) over a period of about 2 hours to about 6 hours. A suitable amount of a cross-linking agent is that amount which will permit intramolecular cross-linking to stabilize the Hb and also intermolecular cross-linking to form polymers of Hb, to thereby increase intravascular retention. Typically, a suitable amount of a cross-linking agent is that amount wherein the molar ratio of cross-linking agent to Hb is in excess of about 2:1. Preferably, the molar ratio of cross-linking agent to Hb is between about 20:1 to 40:1.

Examples of suitable cross-linking agents include polyfunctional agents that will cross-link Hb proteins, such as glutaraldehyde, succindialdehyde, activated forms of polyoxyethylene and dextran, α-hydroxy aldehydes, such as glycolaldehyde, N-maleimido-6-aminocaproyl-(2'-nitro,4'-sulfonic acid)-phenyl ester, m-maleimidobenzoic acid-N-hydroxysuccinimide ester, succinimidyl 4-(N-maleimidomethyl)cyclohexane-1-carboxylate, sulfosuccinimidyl 4-(N-maleimidomethyl)cyclohexane-1-carboxylate, m-maleimidobenzoyl-N-hydroxysuccinimide ester, m-maleimidobenzoyl-N-hydroxysulfosuccinimide ester, N-succinimidyl(4-iodoacetyl)aminobenzoate, sulfosuccinimidyl(4-iodoacetyl)aminobenzoate, succinimidyl 4-(p-maleimidophenyl)butyrate, sulfosuccinimidyl 4-(p-maleimidophenyl)butyrate, 1-ethyl-3-(3-dimethylaminopropyl)carbodiimide hydrochloride, N,N'-phenylene dimaleimide, and compounds belonging to the bis-imidate class, the acyl diazide class or the aryl dihalide class, among others.

Poly(Hb) is defined as having significant intramolecular cross-linking if a substantial portion (e.g., at least about 50%) of the Hb molecules are chemically bound in the poly(Hb), and only a small amount, such as less than about 15%, are contained within high molecular weight poly(Hb) chains. High molecular weight poly(Hb) molecules have a molecule weight, for example, above about 500,000 Daltons.

In a preferred embodiment, glutaraldehyde is used as the cross-linking agent. Typically, about 10 to about 70 grams of glutaraldehyde are used per kilogram of oxidation-stabilized deoxy-Hb. More preferably, glutaraldehyde is added over a period of five hours until approximately 29–31 grams of glutaraldehyde are added for each kilogram of oxidation-stabilized deoxy-Hb.

Wherein the cross-linking agent used is not an aldehyde, the poly(Hb) formed is generally a stable poly(Hb). Wherein the cross-linking agent used is an aldehyde, the poly(Hb) formed is generally not stable until mixed with a suitable reducing agent to reduce less stable bonds in the poly(Hb) to form more stable bonds. Examples of suitable reducing agents include sodium borohydride, sodium cyanoborohydride, sodium dithionite, trimethylamine, t-butylamine, morpholine borane and pyridine borane. The poly(Hb) solution is optionally concentrated by ultrafiltration until the concentration of the poly(Hb) solution is increased to between about 75 and about 85 g/l. For example, a suitable ultrafilter is a 30,000 Dalton filter (e.g., Millipore Helicon Cat # CDUF050LT; Amicon Cat # 540430).

The pH of the poly(Hb) solution is then adjusted to the alkaline pH range to preserve the reducing agent and to prevent hydrogen gas formation, which can denature Hb during the subsequent reduction. The poly(Hb) is typically purified to remove non-polymerized hemoglobin. This can be accomplished by dialfiltration or hydroxyapatite chromatography (see, e.g. U.S. Pat. No. 5,691,453, filed Jun. 7, 1995, which is incorporated herein by reference in its entirety). Following pH adjustment, at least one reducing agent, preferably a sodium borohydride solution, is added to the polymerization step typically through the deoxygenation loop. The pH and electrolytes of the stable poly(Hb) can then be restored to physiologic levels to form a stable polymerized hemoglobin-based oxygen carrier, by diafiltering the stable poly(Hb) with a diafiltration solution having a suitable pH and physiologic electrolyte levels.

Suitable methods of cross-linking hemoglobin and preserving the hemoglobin-based oxygen carrier are discussed in detail in U.S. Pat. No. 5,691,452, issued Nov. 25, 1997, which is incorporated herein by reference in its entirety.

Vertebrates that can receive the hemoglobin-based oxygen carrier, formed by the methods of the invention, include mammals, such as humans, non-human primates, dogs, cats, rats, horses, or sheep. Further, vertebrates, that can receive said hemoglobin-based oxygen carrier, include fetuses (prenatal vertebrate), post-natal vertebrates, or vertebrates at time of birth.

A hemoglobin-based oxygen carrier of the present invention can be administered into the circulatory system by injecting the hemoglobin-based oxygen carrier directly and/or indirectly into the circulatory system of the vertebrate, by one or more injection methods. Examples of direct injection methods include intravascular injections, such as intravenous and intra-arterial injections, and intracardiac injections. Examples of indirect injection methods include intraperitoneal injections, subcutaneous injections, such that the hemoglobin-based oxygen carrier will be transported by the lymph system into the circulatory system or injections into the bone marrow by means of a trocar or catheter. Preferably, the hemoglobin-based oxygen carrier is administered intravenously.

The vertebrate being treated can be normovolemic, hypervolemic or hypovolemic prior to, during, and/or after infusion of the hemoglobin-based oxygen carrier. The hemoglobin-based oxygen carrier can be directed into the circulatory system by methods such as top loading and by exchange methods.

A hemoglobin-based oxygen carrier can be administered therapeutically, to treat hypoxic tissue within a vertebrate resulting from many different causes including anemia, shock, and reduced RBC flow in a portion of, or throughout, the circulatory system. Further, the hemoglobin-based oxygen carrier can be administered prophylactically to prevent oxygen-depletion of tissue within a vertebrate, which could result from a possible or expected reduction in RBC flow to a tissue or throughout the circulatory system of the vertebrate. Further discussion of the administration of hemoglobin to therapeutically or prophylactically treat hypoxia, particularly from a partial arterial obstruction or from a partial blockage in microcirculation, and the dosages used therein, is provided in U.S. Pat. No. 5,854,209, filed Mar. 23, 1995, which is incorporated herein by reference in its entirety.

Typically, a suitable dose, or combination of doses of hemoglobin-based oxygen carrier, is an amount which when contained within the blood plasma will result in a total hemoglobin concentration in the vertebrate's blood between about 0.1 to about 10 grams Hb/dl, or more, if required to make up for large volume blood losses.

The invention will now be further and specifically described by the following examples.

EXEMPLIFICATION

EXAMPLE 1

Bench Scale Experiment

The bench-scale experiments were performed in the apparatus shown in the FIGURE. The defibrinated blood sample used in the bench scale experiment was defibrinated by exposure to collagen. Initially, whole blood is diluted approximately 1:1 with isotonic citrate saline buffer. The diluted blood was then concentrated back to produce a Hb level of 10.5 g/dl (approximately a two-fold concentration). The process volume for the diafiltration was 200 ml, therefore approximately 200 ml buffer was added to approximately 200 ml whole blood followed by concentration back to its original volume. This produced approximately 200 ml of membrane permeate. The 200 ml whole blood at a Hb concentration of 10.5 g/dL was then diafiltered against citrate/saline buffer. The time to collect 400 mls permeate volume (2 retentate volumes) was used as a point of comparison for the citrated blood and the defibrinated blood. The time included the time to concentrate the diluted blood back to its original volume (200 ml) and the time to perform the first diafiltration volume (200 ml). The longer the time, the slower the process. Table 1 summarizes the results.

TABLE 1

| Animal Number | Whole Blood Sample | Time to Collect 400 ml Permeate (Hr: Min: Sec) |
| --- | --- | --- |
| 1 | Citrated | 0:25:08 |
| 1 | Defibrinated | 0:51:06 |
| 2 | Citrated | 0:24:47 |
| 2 | Defibrinated | 0:25:15 |
| 3 | Citrated | 0:25:08 |
| 3 | Defibrinated | 0:24:28 |
| 4 | Citrated | 0:30:18 |
| 4 | Defibrinated | 0:15:57 |

As can be seen from Table 1, the time required to collect 400 ml of permeate was between about fifteen minutes and an hour.

EXAMPLE 2

Pilot Scale Experiment

The pilot-scale experiments were performed in the apparatus shown in the FIGURE. The defibrinated blood sample used in the pilot-scale experiment was defibrinated by mechanical agitation. Again, the whole blood is diluted with isotonic citrate saline solution and concentrated, but because of the large volume required for processing in the pilot scale system, the initial whole blood was diluted with a greater than 1:1 ratio of citrate/saline buffer to whole blood. The Hb concentration of the blood during diafiltration is less than 10.5 g/dl (approximately a two-fold concentration). After concentration back to the minimum process volume of the system (approximately 4.5 L), the blood was diafiltered for 5 diafiltration volumes. As in the bench scale experiment, a longer time indicates a slower process. Table 2 summarizes the results.

TABLE 2

| Experiment Number | Whole Blood Sample | Processing Time to Collect 5 Diafiltration Volumes (minutes) |
| --- | --- | --- |
| 1 | Citrated (Control) | 91 |
|   | Defibrinated | 28 |
| 2 | Citrated (Control) | 83 |
|   | Defibrinated | 150 |

EQUIVALENTS

Those skilled in the art will recognize, or be able to ascertain using no more than routine experimentation, many equivalents to the specific embodiments of the invention described herein. These and all other such equivalents are intended to be encompassed by the following claims.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for preparing a hemoglobin solution, comprising the steps of:
   a) defibrinating whole blood, wherein the whole blood comprises red blood cells and a plasma component;
   b) filtering the defibrinated whole blood by diafiltration across a membrane having a permeability limit in a range of between about 0.01 $\mu$m and about 5 $\mu$m, whereby at least a portion of the plasma component is separated from the red blood cells to form a red blood cell suspension; and thereafter
   c) releasing hemoglobin molecules from the red blood cells of the red blood cell suspension by lysing the red blood cells of the red blood cell suspension and isolating the hemoglobin molecules by centrifuging or filtering the lysed red blood cell suspension;
   whereby a hemoglobin solution is formed.

2. The method of claim 1, wherein centrifuging the red blood cell suspension causes at least a portion of the red blood cells to lyse, thereby releasing hemoglobin molecules.

3. The method of claim 2, wherein the released hemoglobin is isolated by centrifugation.

4. The method of claim 2, wherein the released hemoglobin is isolated by filtration.

5. The method of claim 1, wherein the red blood cells are lysed by centrifuging the red blood cell suspension cells that have been separated in step b).

6. The method of claim 1, wherein the red blood cells are lysed hypotonically.

7. The method of claim 1, further comprising the step of deoxygenating the hemoglobin solution.

8. The method of claim 7, wherein the content of an oxyhemoglobin component of the hemoglobin solution is reduced to less than about 20%.

9. The method of claim 7, wherein the oxyhemoglobin component of the hemoglobin solution is reduced to less than about 10%.

10. The method of claim 7, wherein the hemoglobin solution is deoxygenated by chemical scavenging with a reducing agent.

11. The method of claim 10, wherein the reducing agent is selected from the group consisting of N-acetyl-L-cysteine (NAC), cysteine, sodium dithionite or ascorbate.

* * * * *